United States Patent
Burgess et al.

(10) Patent No.: US 11,773,388 B2
(45) Date of Patent: *Oct. 3, 2023

(54) TARGET ENRICHMENT BY UNIDIRECTIONAL DUAL PROBE PRIMER EXTENSION

(71) Applicants: Roche Sequencing Solutions, Inc., Pleasanton, CA (US); Kapa Biosystems, Inc., Wilmington, MA (US)

(72) Inventors: Daniel Burgess, Black Earth, WI (US); Brian Christopher Godwin, Livermore, CA (US); Alexander Lovejoy, Newark, CA (US); Bronwen Miller, Cape Town (ZA); Jo-Anne Elizabeth Penkler, Cape Town (ZA); Joseph Platzer, Oakland, CA (US)

(73) Assignees: Roche Sequencing Solutions, Inc., Pleasanton, CA (US); Kapa Biosystems, Inc., Wilmington, MA (US)

( * ) Notice: Subject to any disclaimer, the term of this patent is extended or adjusted under 35 U.S.C. 154(b) by 227 days.

This patent is subject to a terminal disclaimer.

(21) Appl. No.: 16/907,736

(22) Filed: Jun. 22, 2020

(65) Prior Publication Data
US 2020/0392483 A1    Dec. 17, 2020

Related U.S. Application Data

(63) Continuation of application No. PCT/EP2018/085727, filed on Dec. 19, 2018.
(Continued)

(51) Int. Cl.
*C12N 15/10* (2006.01)
*C12Q 1/6813* (2018.01)
(Continued)

(52) U.S. Cl.
CPC ..... *C12N 15/1034* (2013.01); *C12N 15/1072* (2013.01); *C12Q 1/6813* (2013.01); *C12Q 1/6874* (2013.01); *C12Q 1/6876* (2013.01)

(58) Field of Classification Search
None
See application file for complete search history.

(56) References Cited

U.S. PATENT DOCUMENTS

| 5,624,825 A | 4/1997 | Walker et al. |
|---|---|---|
| 2005/0123956 A1 | 6/2005 | Blume et al. |

(Continued)

FOREIGN PATENT DOCUMENTS

| EP | 0672173 B1 | 8/2002 |
|---|---|---|
| WO | 93/09250 A1 | 5/1993 |

(Continued)

OTHER PUBLICATIONS

Ganova-Raeva et al., "Primer Extension Enrichment Reaction (PEER): a new subtraction method for identification of genetic differences between biological specimens," Nucleic Acids Res. 2006, 34(11):e76. (Year: 2006).*

(Continued)

*Primary Examiner* — Kaijiang Zhang
(74) *Attorney, Agent, or Firm* — Kristen K. Walker; Olga Kay

(57) ABSTRACT

The present disclosure provides a method for enrichment of at least one target nucleic acid in a library of nucleic acids. A first oligonucleotide is hybridized to a target nucleic acid in library of nucleic acids having first and second adapters. The hybridized first oligonucleotide is extended with a first polymerase, thereby producing a first primer extension complex including the target nucleic acid and the extended first oligonucleotide. The first primer extension complex is captured, enriched relative to the library of nucleic acids, and a (Continued)

second oligonucleotide is hybridized to the target nucleic acid. The hybridized second oligonucleotide is extended with a second polymerase, thereby producing a second primer extension complex including the target nucleic acid and the extended second oligonucleotide, and further liberating the extended first oligonucleotide from the first primer extension complex.

12 Claims, 7 Drawing Sheets

Related U.S. Application Data

(60) Provisional application No. 62/609,013, filed on Dec. 21, 2017.

(51) Int. Cl.
  *C12Q 1/6876* (2018.01)
  *C12Q 1/6874* (2018.01)

(56) References Cited

U.S. PATENT DOCUMENTS

| | | | |
|---|---|---|---|
| 2017/0037459 A1* | 2/2017 | Godwin | C12Q 1/6855 |
| 2017/0159040 A1* | 6/2017 | Lock et al. | C12Q 1/6806 |

FOREIGN PATENT DOCUMENTS

| | | | | |
|---|---|---|---|---|
| WO | WO2013169339 | A1 | 11/2013 | |
| WO | 2016149837 | A1 | 9/2016 | |
| WO | WO-2016149837 | A1 * | 9/2016 | C12N 15/1006 |
| WO | 2017021449 | A1 | 2/2017 | |
| WO | 2017/144457 | A1 | 8/2017 | |

OTHER PUBLICATIONS

Wong et al., "Multiplex Illumina Sequencing Using DNA Barcoding," Curr. Protoc. Mol. Biol. 2013, 7.11.1-7.11.11. (Year: 2013).*
International Bureau, on behalf of the International Searching Authority, "International Preliminary Report on Patentability," for International Patent Application No. PCT/EP2018/085727 (dated Jun. 23, 2020).
International Searching Authority, "International Search Report," for International Patent Application No. PCT/EP2018/085727 (dated Jun. 27, 2019).
International Searching Authority, "Written Opinion of the International Searching Authority," for International Patent Application No. PCT/EP2018/085727 (dated Jun. 27, 2019).
Brotherton, et al., "Neolithic mitochondrial haplogroup H genomes and the genetic origins of Europeans," Nature Communications 4:1764 (2013).
Ganova-Raeva, et al., "Primer Extension Enrichment Reaction (PEER): a new subtraction method for identification of genetic differences between biological specimens," Nucleic Acids Research 34(11):e76 (2006).
Ganova-Raeva, "Chapter 6: Primer Extension Enrichment Reaction (PEER) and Other Methods for Difference Screening," from Nucleic Acids Hybridization, pp. 125-165 (2007).
Patel and Sive, "PCR-based subtractive cDNA cloning," Curr. Protoc. Mol. Biol., Chapter 25, Unit 25B.2 (2001).
Ganova-Raeva, L et al, Primer Extension Enrichment Reaction (PEER): a new subtraction method for identification of genetic differences between biological specimens, Nuc Acid Res, (2006), pp. e76, vol. 34 Issue 11.
Ganova-Raeva, L M, Nucleic Acids Hybridization: modern applications, Primer Extension Enrichment Reaction (Peer) and other Methods for Difference Screening, (2007), pp. 125-165, vol. 34 Issue 11, Springer.
International Search Report and Written Opinion, dated Feb. 14, 2019, in corresponding PCT/EP2018/085727, filed Dec. 19, 2018, pp. 1-14.

* cited by examiner

TARGET ENRICHMENT BY UNIDIRECTIONAL DUAL PROBE PRIMER EXTENSION

CROSS-REFERENCE TO RELATED APPLICATIONS

This patent application is a continuation of International Patent Application No. PCT/EP2018/085727 filed Dec. 19, 2018, which claims priority to and the benefit of U.S. Provisional Application No. US 62/609,013, filed Dec. 21, 2017. Each of the above patent applications is incorporated herein by reference as if set forth in its entirety.

FIELD OF THE INVENTION

The disclosure relates generally to enrichment of nucleic acid targets in a sample and more particularly, to enrichment of targets lot nucleic acid sequencing, including high throughput sequencing.

BACKGROUND

The invention belongs to a class of technologies that allow users to focus on regions of interest within the nucleic acid to be sequenced. This lowers costs associated with sequencing reactions and subsequent data analysis. There are currently three general types of technologies that selectively capture regions of interest within a nucleic acid present in a sample. The first technology is hybridization capture wherein regions of interest are captured through the hybridization of a probe that can be selectively bound to a capture surface. This capture allows for the removal of non-target nucleic acids followed by a release and collection of the captured target molecules. This type of technology has advantages including the ability to capture exome-sized regions and regions that contain unknown structural variations. The disadvantages include long and complex protocols that tend to take well over 8 hours to complete. The complexity is primarily caused by the requirement to prepare a randomly fragmented shotgun library prior to hybridization. The hybridization step alone can take up to three days to complete. Examples of this type of technology include SECAP EZ target enrichment system (ROCHE) and SURESELECT target enrichment system (AGILENT).

Another method of target enrichment is dual-target primer based amplification. In this method, regions of interest are enriched using two probes on the boundaries of the target. The methods tend to take less than 8 hours to complete and are simpler than hybridization capture methods. However, dual primer based technologies are not capable of enriching sequences with unknown structural variations. The most established dual primer approach is multiplex polymerase chain reaction (PCR). It is a very simple single step process but is only capable of amplifying tens of targets per reaction tube. Other newer technologies are currently available, including TRUSEQ amplicon sequencing kit (ILLUMINA) and ION TORRENT AMPLISEQ sequencing kit (LIFE TECHNOLOGIES) products which are capable of amplifying hundreds to thousands of targets in a single reaction tube and require only a few handling steps.

The third technology is single-target primer based amplification. In this method, targets are enriched through the amplification of a region that is defined by a single target primer and an end-ligated universal primer. Similar to the hybridization based approach; these technologies require a randomly fragmented shotgun library to be generated prior to the selective hybridization of a target oligonucleotide. However, instead of using this oligonucleotide to capture the target and wash away non-target molecules, an amplification step is employed which selectively amplifies regions between the randomly-generated end and the target specific oligonucleotide. The advantage of this technology is that unlike dual primer technologies, it allows for the detection of sequences with unknown structural variations. It is also faster and simpler than hybridization based technologies. However, this type of technology is still slower anti more complicated than dual printer based approaches. Examples of this type of technology are ARCHER'S Anchored Multiplex PCR (ARCHER DX) and OVATION target enrichment system (NUGEN).

There remains an unmet need for a fast and simple method of target enrichment that would also accommodate for unknown structural variations in a target sequence.

SUMMARY

According to one embodiment, the present disclosure provides a method for enrichment of at least one target nucleic acid in a library of nucleic acids. The method includes hybridizing a first oligonucleotide to a target nucleic acid in a library of nucleic acids. Each of the nucleic acids in the library of nucleic acids having a first end comprising a first adapter and a second end comprising a second adapter. The method further includes extending the hybridized first oligonucleotide with a first polymerase, thereby producing a first primer extension complex comprising the target nucleic acid and the extended first oligonucleotide. The method further includes capturing the first primer extension complex, enriching the first primer extension complex relative to the library of nucleic acids, hybridizing a second oligonucleotide to the target nucleic acid, and extending the hybridized second oligonucleotide with a second polymerase, thereby producing a second primer extension complex comprising the target nucleic acid and the extended second oligonucleotide, thereby liberating the extended first oligonucleotide from the first primer extension complex. The method further includes amplifying the target nucleic acid with a third polymerase, a first amplification primer, and a second amplification primer, the first amplification primer having a 3' end complementary to the first adapter and the second amplification primer having a 3' end complementary to the second adapter.

In one aspect, the method further includes sequencing the amplified target nucleic acid.

In another aspect, the first oligonucleotide comprises a capture moiety.

In another aspect, capturing the first primer extension complex includes capturing the capture moiety on a solid support.

In another aspect, the capture moiety is biotin, and the solid support comprises streptavidin.

In another aspect, the first oligonucleotide is bound to a solid support prior to hybridizing the first oligonucleotide to a target nucleic acid, and hybridizing the first oligonucleotide to the target nucleic acid and extending the hybridized first oligonucleotide with a polymerase thereby captures the first primer extension complex on the solid support.

In another aspect, capturing the first primer extension complex is performed alter extending the hybridized first oligonucleotide.

In another aspect, the method further includes incorporating at least one modified nucleotide into at least one of the extended first oligonucleotide in the first primer extension complex and the extended second oligonucleotide in the second primer extension complex.

In another aspect, the modified nucleotide is selected from dUTP and a nucleotide having a capture moiety.

In another aspect, the method further includes incorporating at least one modified nucleotide into the extended first oligonucleotide in the first printer extension complex, the at least one modified nucleotide having a capture moiety.

In another aspect, capturing the first primer extension complex comprises capturing the capture moiety on a solid support.

In another aspect, the method further includes incorporating at least one uracil into at least one of the extended first oligonucleotide in the first primer extension complex, and the extended second oligonucleotide in the second primer extension complex, thereby forming a uracil-containing oligonucleotide product.

In another aspect, the method further includes digesting the uracil-containing oligonucleotide product.

In another aspect, digesting the uracil-containing oligonucleotide product is achieved with at least one of a uracil DMA glycosylase and a DNA glycosylase-lyase.

In another aspect, the DNA glycosylase-lyase is selected from Endonuclease IV, and Endonuclease VIII.

In another aspect, the method further includes contacting the library of nucleic acids with a blocking oligonucleotide.

In another aspect, the blocking oligonucleotide is at least partially complementary to at least one of the first adapter and the second adapter.

In another aspect, the blocking oligonucleotide is a universal blocking oligonucleotide.

In another aspect, the first adapter and the second adapter have the same nucleic acid sequence.

In another aspect, the first adapter and the second adapter have different nucleic acid sequences.

In another aspect, the first adapter and the second adapter are forked adapters.

In another aspect, the first adapter and the second adapter comprise at least one uracil.

In another aspect, at least one of the first polymerase and the second polymerase is a uracil incompatible polymerase.

In another aspect, the third polymerase is a uracil compatible polymerase.

In another aspect, the second oligonucleotide hybridizes to the target nucleic and at a position 5' to the first oligonucleotide.

In another aspect, the third polymerase is a uracil incompatible polymerase.

In another aspect, at least cine of the first adapter, the second adapter, the first amplification primer, and the second amplification primer comprises at least one of a unique identifier (UID) sequence, a molecular identifier (MID) sequence.

According to another embodiment, the present disclosure provides a kit for enrichment of at least one target nucleic acid in a library of nucleic acids. The kit includes a first oligonucleotide complementary to a target nucleic acid in library of nucleic acids, each of the nucleic acids in the library of nucleic acids having a first end including a first adapter and a second end including a second adapter. The kit further includes a second oligonucleotide complementary to the target nucleic acid, a first amplification primer, and a second amplification primer. The first oligonucleotide comprises a capture moiety, the second oligonucleotide hybridizes to the target nucleic acid at a position 5' to the first oligonucleotide, and the first amplification primer has a 3' end complementary to the first adapter and the second amplification primer has a 3" end complementary to the second adapter.

According to another embodiment, the present disclosure provides a kit for enrichment of at least one target nucleic acid in a library of nucleic acids. The kit includes a first oligonucleotide complementary to a target nucleic acid in library of nucleic acids, each of the nucleic acids in the library of nucleic acids having a first end including a first adapter and a second end including a second adapter. The kit further includes a modified nucleotide having a capture moiety, a second oligonucleotide complementary to the target nucleic acid, a first amplification primer, and a second amplification primer. The second oligonucleotide hybridizes to the target nucleic acid at a position 5" to the first oligonucleotide, and the first amplification primer has a 3' end complementary to the first adapter and the second amplification primer has a 3' end complementary to the second adapter.

In one aspect, the kit further includes at least one of a uracil nucleotide, a uracil compatible polymerase, a uracil incompatible polymerase, and a blocking oligonucleotide.

According to another embodiment, the present disclosure provides a composition including a library of nucleic acids including at least one target nucleic acid. Each of the nucleic acids in the library of nucleic acids has a first end comprising a first adapter, a second end comprising a second adapter, and a region of interest intermediate the first adapter and the second adapter. The composition further includes an extended first oligonucleotide hybridized to the region of interest of the target nucleic acid. The extended first oligonucleotide includes at least one capture moiety. The composition further includes a solid support bound to the at least one capture moiety, a second oligonucleotide hybridized to the target nucleic acid at a position 5' to the first extended oligonucleotide, and polymerase associated with a 3' end of the second oligonucleotide.

In one aspect, the composition further includes a blocking oligo hybridized with each of the first adapter and the second adapter.

In another aspect, the at least one capture moiety is located at a 5' end of the extended first oligonucleotide.

In another aspect, at least one capture moiety is incorporated into at an extended portion of the extended first oligonucleotide.

In another aspect, the extended first oligonucleotide further comprises at least one uracil and at least one thymine.

In another aspect, the polymerase is a uracil incompatible polymerase.

In another aspect, at least one of the first adapter and the second adapter comprise at least one uracil and at least one thymine.

In another aspect, liberating the extended first oligonucleotide from the first primer extension complex is achieved with an enzyme having an activity selected from strand-displacing activity, a 5' to 3' exonuclease activity, and a flap endonuclease activity.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2A illustrates a first oligonucleotide 208 hybridized to the target nucleic acid 200. FIG. 2B illustrates that hybridized oligonucleotide 208 is extended with a first polymerase. FIG. 2C illustrates a second oligonucleotide 220 hybridized to the target nucleic acid 200. FIG. 2D illustrates that hybridized second oligonucleotide 220 is extended with a second polymerase. FIG. 2E illustrates that target nucleic acid 200 is amplified.

FIG. 3A illustrates a first oligonucleotide 308 hybridized to the target nucleic acid 300 and captured on a solid support 318. FIG. 3B illustrates that the first oligonucleotide 308 is extended with a first polymerase.

FIG. 4A illustrates a first oligonucleotide 408 hybridized to the target nucleic acid 400. FIG. 4B illustrates that the hybridized first oligonucleotide 408 is extended with a first polymerase. FIG. 4C illustrates a second oligonucleotide 420 hybridized to the target nucleic acid 400. FIG. 4D illustrates that the target nucleic acid 400 is amplified with a third polymerase.

DETAILED DESCRIPTION

I. Definitions

Figure 1:
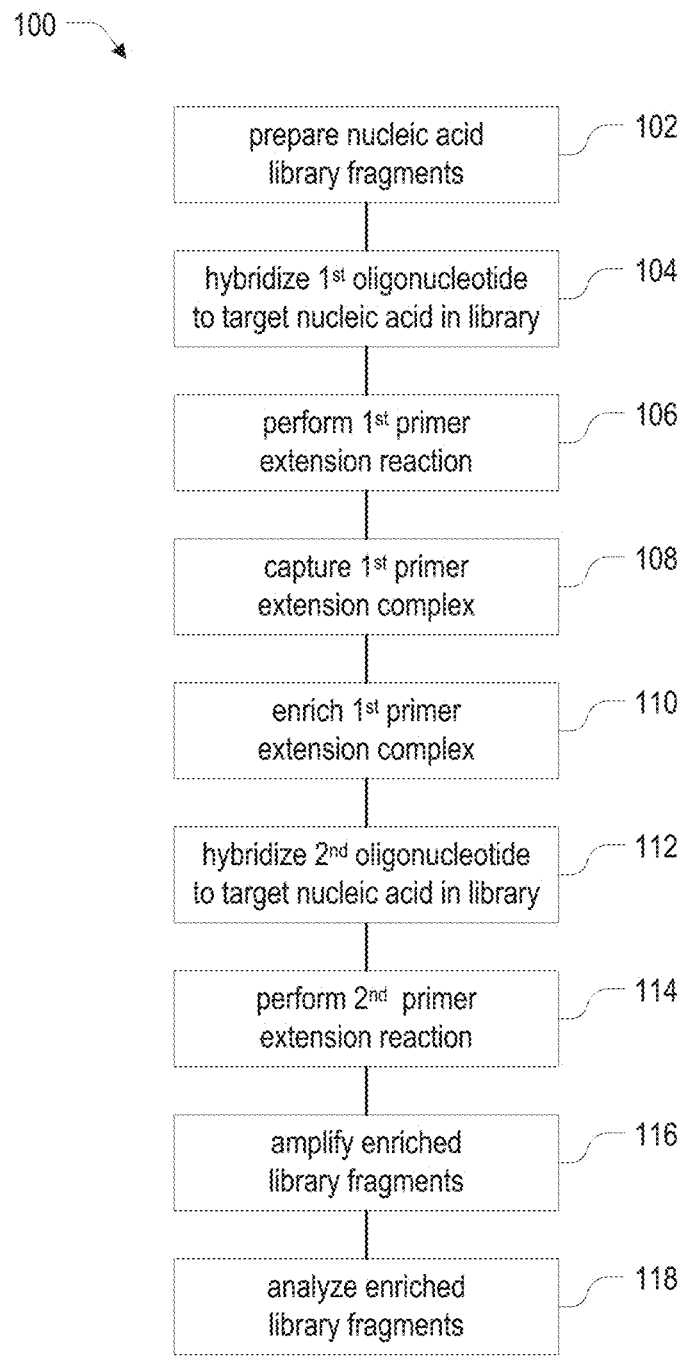
FIG. 1 is a schematic flow diagram illustrating an embodiment of a method for enrichment of at least one target nucleic acid in a library of nucleic acids according to the present disclosure.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or mote additional components or steps, and (iv) the terms "about" and "approximately" may be understood to permit standard variation as would be understood by those of ordinary skill in the art; and (v) where ranges are provided, endpoints are included.

Adapter: As used herein, "adapter" means a nucleotide sequence that may be added to another sequence so as to import additional properties to that sequence. An adapter can be single- or double-stranded, or may have both a single-stranded portion and a double-stranded portion.

Approximately: As used herein, the term "approximately" or "about", as applied to one or more values of interest, refers to a value that is similar to a stated reference value. In certain embodiments, the term "approximately" or "about" refers to 3 range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level, and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Barcode: As used herein, "barcode" means a nucleotide sequence conferring identity to a molecule. A barcode may confer a unique identity to an individual molecule (and its copies). Such a barcode is a unique ID (UID). A barcode may confer an identity to an entire population of molecules (and their copies) coming from the same source (e.g., a patient). Such a barcode is a multiplex ID (MID).

Biological Sample: As used herein, the term "biological sample" typically refers to a sample obtained or derived from a biological source (e.g., a tissue or organism or cell culture) of interest, as described herein. In some embodiments, a source of interest comprises or consists of an organism, such as an animal or human. In some embodiments, a biological sample comprises or consists of biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample comprises or consists of cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Blocking oligonucleotide: an oligonucleotide complementary to another nucleic acid present in the reaction mixture and capable of hybridizing to such nucleic acid to prevent undesirable hybridization of such nucleic acid. Such another nucleic acid can be a synthetic nucleic acid, e.g., a primer or an adapter. The undesirable hybridization to be prevented may occur when the primer or adapter are incorporated into a library nucleic acid molecule. The blocking oligonucleotide need not be perfectly complementary to the nucleic acid to be protected from undesirable hybridization but must form a stable enough hybrid to prevent the undesirable events from occurring. To that end, the blocking oligonucleotide may comprise universal bases or $T_m$-modified bases.

Comprising: A composition or method described herein as "comprising" one or more named elements or steps is open-ended, meaning that the named elements or steps are essential, but other elements or steps may be added within the scope of the composition or method. It is to be understood that composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Designed: As used herein, the term "designed" refers to an agent (i) whose structure is or was selected by the hand of man; (ii) that is produced by a process requiring the hand of man; and/or (iii) that is distinct from natural substances and other known agents.

Determine: Those of ordinary skill in the art, reading the present specification, will appreciate that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Ligation Site: As used herein, "ligation site" is a portion of a nucleic acid molecule (other than a blunt end of a double stranded molecule) that can facilitate ligation. "Compatible ligation sites" present on two molecules enable preferential ligation of the two molecules with each other.

Sample: As used herein, the term "sample" refers to a substance that is or contains a composition of interest for qualitative and or quantitative assessment. In some embodiments, a sample is a biological sample (i.e., comes from a living thing (e.g., cell or organism). In some embodiments, a sample is from a geological, aquatic, astronomical, or agricultural source. In some embodiments, a source of interest comprises or consists of an organism, such as an animal or human. In some embodiments, a sample for forensic analysis is or comprises biological tissue, biological fluid, organic or non-organic matter such as, e.g., clothing, dirt, plastic, water. In some embodiments, an agricultural sample, comprises or consists of organic matter such as leaves, petals, bark, wood, seeds, plants, fruit, etc.

Single-Stranded Ligation: As used herein, "single-stranded ligation" is a ligation procedure commencing with at least one single-stranded substrate and typically involving one or more double-stranded or partially-double-stranded adapters.

Solid support: As used herein, "solid support" refers to any solid material capable of interacting with a capture moiety. A solid support can be a solution-phase support capable of suspension in a solution (e. g., a glass bead, a magnetic bead, or another like particle), or a solid-phase support (e.g., a silicon wafer, a glass slide, or the like). Examples of solution-phase supports include superparamagnetic spherical polymer particles such as DYNABEADS magnetic beads from INVITROGEN or magnetic glass panicles such as described in U.S. Pat. Nos. 656,568, 6,274,386, 7,371,830, 6,870,047, 6,255,477, 6,746,874 and 6,258,531.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Synthetic: As used herein, the word "synthetic" means produced by the hand of man, and therefore in a form that does not exist in nature, either because it has a structure that does not exist in nature, or because it is either associated with one or more other components, with which it is not associated in nature, or not associated with one or more other components with which it is associated in nature.

Universal Primer: As used herein, "universal primer" and "universal priming site" refer to a primer and priming site not naturally present in the target sequence. Typically, the universal priming site is present in adapters or target-specific primers. The universal primer can bind to and direct primer extension from the universal priming site.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, a variant may also have one or more functional defects and/or may otherwise be considered a "mutant". In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

II. Detailed Description of Certain Embodiments

For many nucleic acid enrichment technologies, it can be useful to first provide a shotgun library of nucleic acids, whereby longer nucleic acids sequences derived from a sample are subdivided into smaller fragments that are compatible with short read sequencing technologies (i.e., about 50-500 nucleotides). To prepare a shotgun library, a high-molecular-weight nucleic acid strand (typically cDNA or genomic DNA) is sheared into random fragments, optionally modified through ligation of common end sequences (i.e., adapters), and size-selected for downstream processing and analysis. For example, it may be useful to selectively capture a subset of the nucleic acids in the shotgun library.

Currently, there exist two general categories of capture technologies: hybridization based capture and amplification-based capture. Hybridization-based capture methods offer the advantage of enabling recovery of the entirety of the original shotgun library fragment as opposed to replicating and recovering only a subset of the original library fragment. However, on-target rates associated with hybridization-based capture are generally lower in comparison with amplification-based methods. Notably, a lower on-target rate results in wasted sequencing capacity due to the necessity to sequence off-target capture product. Moreover, workflows associated with hybridization-based capture methods can be complex with long turnaround times relative to amplification-based approaches. By contrast, while amplification-based approaches such as anchored multiplex PCR methods offer the advantages of simple workflows, faster turnaround times and higher on-target rates relative to hybridization-based methods, there remain several disadvantages. For example, target-specific primer sequences incorporated into library fragments following amplification result in wasted sequencing capacity. Moreover, library fragments are not necessarily representative of the original shotgun library as the template is necessarily truncated at the target specific primer binding site. Accordingly, there remains an unmet need for a fast and simple method of target enrichment that would also accommodate for unknown structural variations in a target sequence.

These and other challenges may be overcome with a method for target enrichment by unidirectional dual probe primer extension according to the present disclosure. In one aspect, the present disclosure describes both a general approach for unidirectional dual probe primer extension based enrichment as well as improvements therefor. To this end, the present disclosure provides for a combination of primer extension and hybridization-based capture onto a solid support for enrichment of one or more target nucleic acids from a library of target nucleic acids. The present disclosure further provides for an overall workflow having many of the aforementioned advantages of anchored multiplex amplification-based enrichment methods and hybridization capture methods without many of the aforementioned disadvantages. Advantages of the kits, compositions and methods of the present disclosure include recovery of library molecules derived from the entire shotgun molecule, simple workflows (e.g., fewer total steps and less hands-on time), fast turnaround times, higher on target rates, and lower overall material costs relative to many existing hybridization-based capture methods and anchored multiplex amplification based capture methods.

In one embodiment, the invention is a method for enrichment of at least one target nucleic acid in a library of nucleic acids. The method can include hybridizing a first oligonucleotide to a target nucleic acid in the library of nucleic acids. Each of the nucleic acids in the library of nucleic acids can be provided with a first end comprising a first adapter and a second end comprising a second adapter. The method further includes extending the hybridized first oligonucleotide with a first polymerase, thereby producing a first primer extension complex including the target nucleic acid and the extended first oligonucleotide.

In one aspect, the method can further include capturing the first primer extension complex and enriching the first primer extension complex relative to the library of nucleic acids. In another aspect, the method can include hybridizing a second oligonucleotide to the target nucleic acid, and extending the hybridized second oligonucleotide with a second polymerase, thereby producing a second primer extension complex comprising the target nucleic acid and the extended second oligonucleotide, thereby liberating the extended first oligonucleotide from the first primer extension complex. The method can further include amplifying the target nucleic acid with a third polymerase, a first amplification primer, and a second amplification primer. The first amplification primer having a 3' end complementary to the first adapter and the second amplification primer having a 3' end complementary to the second adapter.

The first, second, and third polymerase can be any suitable polymerase. One example polymerase is a Taq or Taq-derived polymerase (e.g., KAPA 2G polymerase from KAPA BIOSYSTEMS). Another example polymerase is a B-family DNA polymerase (e.g., KAPA HIFI polymerase from KAPA BIOSYSTEMS).

In another embodiment, the present disclosure provides for a kit for enrichment of at least one target nucleic acid in a library of nucleic acids. The kit can include a first oligonucleotide complementary to a target nucleic acid in the library of nucleic acids. Each of the nucleic acids in the library of nucleic acids has a first end comprising a first adapter and a second end comprising a second adapter. The kit can further include a second oligonucleotide complementary to the target nucleic acid, a first amplification primer, and a second amplification primer. The first oligonucleotide can include a capture moiety. The second oligonucleotide can hybridize to the target nucleic acid at a position 5' to the first oligonucleotide. The first amplification primer has a 3' end complementary to the first adapter and the second amplification primer has a 3' end complementary to the second adapter.

In another embodiment, the present disclosure provides for a kit for enrichment of at least one target nucleic acid in a library of nucleic acids. The kit can include a first oligonucleotide complementary to a target nucleic acid in library of nucleic acids. Each of the nucleic acids in the library of nucleic acids can have a first end comprising a first adapter and a second end comprising a second adapter. The kit can further include a modified nucleotide having a capture moiety, a second oligonucleotide complementary to the target nucleic acid, a first amplification primer, and a second amplification primer. The second oligonucleotide hybridizes to the target nucleic acid at a position 5' to the first oligonucleotide, and the first amplification primer has a 3" end complementary to the first adapter and the second amplification primer has a 3' end complementary to the second adapter.

In yet another embodiment, the present disclosure provides for a composition, including a library of nucleic acids including at least one target nucleic acid. Each of the nucleic acids in the library of nucleic acids have a first end comprising a first adapter, a second end comprising a second adapter, and a region of interest intermediate the first adapter and the second adapter. The composition further includes an extended first oligonucleotide hybridized to the region of interest of the target nucleic acid. The extended first oligonucleotide includes at least one capture moiety. The composition further includes a solid support bound to the at least one capture moiety, a second oligonucleotide hybridized to the target nucleic acid at a position 5' to the first extended oligonucleotide, and a polymerase associated with a 3' end of the second oligonucleotide.

The methods of the instant invent ion can be used as a part of a sequencing protocol, including a high throughput single molecule sequencing protocol. The method of the invention generates a library of target nucleic acids to be sequenced. The target nucleic acids in the library may incorporate barcodes for molecular identification and sample identification.

The present invention comprises at least one linear primer extension step with a target specific primer. The linear extension step has several advantages over exponential amplification practiced in the art. Each target nucleic acid is characterized by a unique rate of synthesis that depends on the rate of annealing of the target-specific primer and the rate with which a polymerase can read through a particular target sequence. Differences in the rate of extension and the rate of synthesis create a bias that may result in a slight difference in a single round of synthesis. However, the slight difference becomes exponentially amplified during PCR. The resulting gap is referred to as PCR bias. The bias may obscure any difference in the initial quantities of each sequence in the sample and preclude any quantitative analysis.

The present invention limits extension of target-specific primers (including gene-specific primers and degenerate primers that by chance are specific to a binding site within the genome) to a single step. Any exponential amplification is performed with universal primers not subject to template-dependent bias, or subject to a lesser bias than the target-specific primer.

Referring now to FIG. 1, a method 100 for target enrichment by unidirectional dual probe primer extension includes a step 102 of preparing nuclease acid library fragments. In one aspect the nucleic acid library fragments can be prepared from any source of nucleic acids including one or more target nucleic acids. In general, a target nucleic acid will include a region or sequence of interest, and the method 100 enables the preferential enrichment of the one or more target nucleic acids relative to non-target nucleic acids in the nucleic acid library for downstream detection and analysis of those regions or sequences of interest.

With continued reference to the step 102, the nucleic acids are optionally fragmented and adapters are ligated to each end of the nucleic acids. Example methods for preparing libraries of nucleic acid fragments for use with the present disclosure include transposon-mediated fragmentation and labeling, mechanical shearing, enzymatic digestion, overhang (e.g., T/A) or blunt end ligation, template-switching mediated adapter ligation, the tike and combinations thereof. Ultimately, the product of the step 102 of preparing nucleic acid library fragments can result in a library of nucleic acids, where each of the nucleic acids in the library of nucleic acids has a first end comprising a first adapter and a second end composing a second adapter. Notably the first and second adapter can be the same or different and can further take on various morphologies including, but not limited to, forked or Y-shaped adapters having a complementary portion and a non-complementary portion, blunt end adapters, overhang adapters, hairpin adapters, the like, and combinations thereof. In general, at least a portion of the aforementioned adapters are double-stranded; however, other adapter configurations can also be used in preparing a library of nucleic acid fragments according to the present disclosure. Moreover, in the case of hairpin adapters, it may be useful to include a blocking element (e.g., a 3' dideoxynucleotide or phosphate group) to prevent self-priming events.

A next step 104 of the method 100 can include hybridization of a first oligonucleotide primer to a target nucleic acid present in the library of nucleic acids, thereby forming an unextended first primer-target complex. In one embodiment, the first oligonucleotide primer is a target-specific primer having a defined sequence that is complementary to a sequence of a target nucleic acid. One example of a target-specific primer is a gene-specific primer designed to hybridize to or nearby (e.g., upstream of, or 5' to) a gene (e.g., cDNA, genomic DNA) of interest. The target nucleic acid can be RNA, DNA, or a combination thereof. The first oligonucleotide primer can be an oligonucleotide primer composed of ribonucleic acids, deoxyribonucleic acids, modified nucleic acids (e.g., biotinylated, locked nucleic acids, inosines, Seela bases, or the like), or other nucleic acid analogs known in the art.

In various embodiments of the present disclosure, the first oligonucleotide primer can include one or more modified bases, capture moieties or a combination thereof in the case that the first oligonucleotide primer includes a capture moiety, the first oligonucleotide primer can be attached to a solid support or be free in solution (i.e., not bound or otherwise attached to a solid support) prior to the step 104 of hybridizing the first oligonucleotide primer to the target nucleic acid. In embodiments where the first oligonucleotide primer including a capture moiety is not attached to a solid support via the capture moiety, the step 104 can be carried out in solution. In embodiments where the first oligonucleotide primer including a capture moiety is attached to a solid support via the capture moiety, the step 104 can be carried out in situ. Notably, in the case of an in situ reaction, the resulting unextended primer-target complex will be attached to a solid support. Any non-target nucleic acids or target nucleic acids not annealed to the first oligonucleotide primer that remain in solution can be removed by separating the solution from the solid support to which primer-target complexes are bound.

A next step 106 of the method 100 includes performing a first primer extension reaction. In one aspect, the step 106 includes extension of the hybridized first oligonucleotide primer with a first polymerase. Following hybridization of the first oligonucleotide primer to the target nucleic acid template in the step 104, the first oligonucleotide primer is extended by the first polymerase, thereby generating a first primer extension product or complex including a 3' region of the extended first oligonucleotide primer comprising the reverse complement of at least a portion of the target nucleic acid template. As described herein, the hybridization and extension reactions are optionally performed simultaneously, whereas in other embodiments, the hybridization and extension reactions are performed separately (e.g., sequentially) and may be separated by a wash step removing the non-annealed and not captured target nucleic acids from the reaction mixture. Moreover, the step 104 can further include termination of the primer extension reaction in order to control the length of the extended first oligonucleotide primer. Notably, the length of the extended first oligonucleotide primer product can be controlled actively through techniques such as inactivating the polymerase added in the step 104, or passively by enabling the reaction to go to completion such as through the consumption of limiting reactants or by controlling/selecting the size of the fragments of the nucleic acids in the library of nucleic acids in the step 102 of the method 100.

The method 100 further includes a step 108 of capturing the first primer extension complex. Capture of the first primer extension complex can be achieved in a variety of ways as disclosed herein and can be achieved prior to, concurrent with, or subsequent to either of the step 104 and the step 106 of the method 100. As described above, the first oligonucleotide can include a capture moiety that can be used to capture the first oligonucleotide primer onto a solid support before, during, or after the step 104 or the step 106 of the method 100. In another example, extension of the first oligonucleotide primer following hybridization to the target nucleic acid includes incorporation of one or more modified nucleotides. The modified nucleotides can include a capture moiety or may be configured to enable downstream modification of the modified nucleotides to attach or otherwise incorporate a capture moiety into the extended portion of the first primer extension complex. Accordingly, the first primer extension complex can be captured during or subsequent to the step 106 by way of the capture moieties associated with the one or more modified nucleotides. The choice of whether the target nucleic acid, the annealed primer-target complex, or the target-extended primer complex is captured further determines whether the step 104 and the step 106 of the method are performed in solution or in situ.

A next step 110 of the method 100 can include enrichment of the 1$^{st}$ primer extension complex. In one aspect, the step 110 includes one or more purification and enrichment steps for recovery of the first primer extension complex front non-target nucleic acids in the library and other molecules such as unused reaction components (e.g., nucleotides, primer molecules, ATP, etc.), enzymes, buffers, or the like. In some embodiments, the step 110 includes enzymatic digestion, size-exclusion based purification, affinity-based purification, the like, or a combination thereof. Notably, enrichment of the first primer extension product can be measured relative to the totality of the library of nucleic acids. In one aspect, enrichment involves increasing the concentration of the target nucleic acid through depletion (i.e., removal) of other members of the library of nucleic acids that are not target nucleic acids.

A next step 112 of the method 100 can include hybridization of a second oligonucleotide primer to a target nucleic acid present in the library of nucleic acids. In one aspect, the second oligonucleotide primer is a target specific primer that binds to a region of interest within the target nucleic acid (as opposed to hybridizing with or being complementary to one or both of the first adapter and the second adapter). In another aspect, the target nucleic is a part of the first primer extension complex during the step 112. For example, the second oligonucleotide primer can hybridize to the target nucleic acid at a 5' position (i.e., upstream) relative to the extended first oligonucleotide primer in the first primer extension complex. The resulting unextended second primer-target complex in this case includes the first extended oligonucleotide primer, the target nucleic acid hybridized to the first extended oligonucleotide primer, and the second (unextended) oligonucleotide primer. In the case that the first primer extension product is attached to a solid support during the step 112, the unextended second primer-target complex will similarly be attached to the solid support. In other embodiments, (e.g., after removal of the non-target nucleic acids from the reaction mixture) the first primer extension product is freed from the solid support and is in solution to enable in solution hybridization of the second oligonucleotide primer in the step 112.

A next step 114 of the method 100 includes performing a second primer extension reaction. Following hybridization of the second oligonucleotide primer to the target nucleic acid template in the step 112, the second oligonucleotide primer is extended by a second polymerase, thereby generating a second primer extension product or complex including the target nucleic acid. The extended second oligonucleotide primer includes a 3' region comprising the reverse complement of at least a portion of the target nucleic acid template. In one aspect, extension of the second oligonucleotide primer with the second polymerase liberates the extended first oligonucleotide primer from the complex with the target nucleic acid. Liberating the extended first oligonucleotide from the first primer extension complex can include one or more of strand displacement (e.g., by a polymerase), or digestion (e.g., by a nuclease). For example, liberating the extended first oligonucleotide can be achieved with an enzyme having at least one of a strand-displacing activity, a 5' to 3' exonuclease activity, and a flap endonuclease activity.

As described herein, the step 112 and the step 114 are optionally performed simultaneously, whereas in other embodiments, the step 112 and the step 114 performed separately (e.g., sequentially). Moreover, the step 114 can further include termination of the primer extension reaction in order to control the length of the extended second oligonucleotide primer. Notably, the length of the extended second oligonucleotide primer product can be controlled actively through techniques such as inactivating the polymerase added in the step 114, or passively by enabling the reaction to go to completion such as through the consumption of limiting reactants or by controlling/selecting the size of the fragments of the nucleic acids in the library of nucleic acids.

In the case that the extended first primer included one or more capture moieties attached to a solid support, liberation of the extended first oligonucleotide in the step 114 results in a second primer extension complex that is free in solution as opposed to being attached to a solid support. Accordingly, as described in the step 110 of the method 100, one or more purification techniques can be implemented following the step 114 in order to recover the unbound second extension product or complex including the target nucleic acid from the support-attached first extended oligonucleotide primer, the second polymerase, other reaction components, the like, and combinations thereof.

The method 100 further includes a step 116 of amplification. The step 116 can involve linear or exponential amplification (e.g., PCR). In general, the step 116 includes amplifying the target nucleic acid with a third polymerase, a first amplification primer, and a second amplification primer. In one aspect, the first and second amplification primers are designed to be complementary to the sequences of the adapters incorporated into the target nucleic acids in the library of nucleic acids in the step 102. For example, the first amplification primer can have a 3' end complementary to the first adapter and the second amplification primer can have a 3' end complementary to the second adapter. However, the primers for amplification can include any sequences that are present within the target nucleic acid being amplified (e.g., gene/target specific primers, universal primers, or the like) and can support synthesis of one or both strands (i.e., both the top and bottom strands of a double-stranded nucleic acids corresponding to the template of the amplification reaction).

In some embodiments, the step 116 enables selective amplification of the target nucleic acids from the library of nucleic acids as opposed to amplification of either of the first or second extended oligonucleotide primers derived from the target nucleic acid. In one example, a uracil compatible polymerase and dUTP are included in one or both of the extension reactions carried out in the step 106 and the step 114. The extended oligonucleotide primers resulting from the reaction will include at least one uracil nucleotide, whereas the target nucleic acid template can be a DNA template having no uracil nucleotides. Thereafter, a uracil incompatible polymerase is included in the step 116 for amplification of the target nucleic acid. The uracil incompatible polymerase can amplify the target nucleic acid having no uracil nucleotides; however, the uracil incompatible polymerase will be incapable of replicating the uracil-containing extended oligonucleotide primers. Alternatively, or in addition, uracil-containing products can be selectively digested or otherwise degraded, thereby leaving behind only the original molecules from the library of nucleic acids.

After the step 116 of amplification, the method 100 can include a step 118 of analyzing the amplified target nucleic acids. The step 116 can include any method for determining the nucleic acid sequence of one or more products of the method 100. The step 116 can further include sequences alignment, identification of sequence variations, counting of unique primer extension products, the like, or combinations thereof.

In addition to the elements of the present disclosure outlined in the method 100, it can be useful to take into account a number of additional considerations when implementing the kits, compositions, and methods described herein. In one aspect, the primer hybridization step is mediated by the target-specific region of the primer. In some embodiments, the target-specific region is capable of hybridizing to a region of a gene located in an exon, intron, or an untranslated portion of a gene or in an untranscribed portion of the gene (e.g., a promoter or an enhancer). In some embodiments, the gene is a protein-coding gene but in other embodiments, the gene is not a protein-coding gene, such as an RNA-coding gene or a pseudogene. In yet other embodiments, the target-specific region is located in an intergenic region. For mRNA or cDNA targets, the primer may comprise an oligo-dT sequence.

Instead of a pre-designed target-specific region, a primer may contain a degenerate sequence (i.e., a string of randomly incorporated nucleotides). Such a primer may also find a binding site within the genome and act as a target-specific primer for that binding site. Notably, a fully degenerate primer where each nucleotide position is degenerate may not be useful for targeted enrichment. However, partially degenerate primer where only a portion of the nucleotide positions are degenerate may be useful for use according to the present disclosure. For example, primers having partial degeneracy at a single nucleotide position can be useful for the capture of target sequences including one or more single nucleotide polymorphisms (SNP).

In addition to the target-specific region, the primer may comprise additional sequences. In some embodiments, these sequences are located to the 5'-end of the target-specific region. In other embodiments, it may be possible to include these sequences elsewhere within the primer as long as the target-specific region is capable of hybridizing to the target and driving the primer extension reaction as described below. The additional sequences within the primer may include one or more barcode sequences, such as a unique molecular identification sequence (UID) or a multiplex sample identification sequence (MID). The barcode sequences may be present as a single sequence or as two or more sequences.

In some embodiments, the additional sequences include sequences that facilitate ligation to the 5'-end of the primer. The primer may contain a universal ligation sequence that enables ligation of an adapter as described in the following section.

In some embodiments, the additional sequences include one or more a binding sites for one or more universal amplification primers.

The primer extension step is performed by a nucleic acid polymerase. Depending on the type of nucleic acid being analyzed, the polymerase may be a DNA-dependent DNA polymerase ("DNA polymerase") or an RNA-dependent DNA polymerase ("reverse transcriptase").

In some embodiments it is desired to control the length of the nucleic acid strand synthesized in the primer extension reaction. As is explained below, the length of this strand determines the length of the nucleic acid subjected to the subsequent steps of the method and any downstream applications. The extension reaction can be terminated by any method known in the art. For example, the reaction may be physically stopped by a shift in temperature or addition of a polymerase inhibitor. In some embodiments, the reaction is stopped by placing the reaction on ice. In other embodiments, the reaction is stopped by elevating the temperature to inactivate a non-thermostable polymerase. In yet other embodiments, the reaction is stopped by the addition of a chelator, such as EDTA able to sequester a critical co-factor for the enzyme, or another chemical or biological substance compound able to reversibly or irreversibly inactivate the enzyme.

Another method of controlling the length of primer extension products is starving the extension reaction by limiting a critical component (e.g., dNTPs) to directly limit the extension length or $Mg^{2+}$ to slow the rate of extension and improve the capability to control the extension stop point. One skilled in the art is able to experimentally or theoretically determine the proper amount of the critical component that allows for limited primer extension to yield predominantly the desired-length product.

Another method of controlling the length of primer extension products is the addition of terminator nucleotides, including reversible terminator nucleotides. One skilled in the art is able to experimentally or theoretically determine a proper ratio of terminator and non-terminator nucleotides that allows for limited primer extension to yield predominantly the desired length product. Examples of terminator nucleotides include dideoxynucleotides, 2'-phosphate nucleotides as described in U.S. Pat. No. 8,163,487 to Gelfand et al., 3'-O-blocked reversible terminators, and 3' unblocked reversible terminators as described e.g., in U.S. Pat. App. Pub. No. 2014/0242579 to Zhuo et al., and Guo, J., et al., Four-color DNA sequencing with 3'-O-modified nucleotide reversible terminators and chemically cleavable fluorescent dideoxynucleotides, P.N.A.S. 2008 105 (27) 9145-9150. Yet another method of controlling the length of primer extension products is the addition of limited amounts of uracil (dUTP) to the primer extension reaction. The uracil-containing DNA can then be treated with uracil-N-DNA glycosylase to produce abasic sites. The DNA with abasic sites can be degraded by heat treatment with optional addition of alkali to improve the efficiency of degradation as described in U.S. Pat. No. 8,669,061 to Gupta et al. One skilled in the art is able to experimentally or theoretically determine a proper ratio of dUTP to dTTP in the extension reaction that allows for limited inclusion of dUTP to yield predominantly the desired length product upon endonuclease treatment.

In some embodiments, the length of the extension product is intrinsically limited by the length of the input nucleic acid. For example, cell-free DNA present in maternal blood plasma is below 200 bp in length with the majority being 166 bp long. Yu, S. C. Y. et al., Size-based molecular diagnostics using plasma DNA for noninvasive prenatal testing, PNAS USA 2014; 111(23):8583-8. The median length of cell-free DNA found in the plasma of healthy individuals and cancer patients is about 185-200 bp. Giacona, M. B., et al., Cell-free DNA in human blood plasma: length measurements in patients with pancreatic cancer and healthy controls, Pancreas 1998; 17(1); 89-97. Poorly preserved or chemically treated samples may contain chemically or physically degraded nucleic acids. For example, formalin-fixed paraffin embedded tissues (FFPET) typically yield nucleic acids that average 150 bp in length.

In some embodiments, the method of the invention includes one or more purification steps after the primer extension by DNA polymerase or reverse transcriptase. The purification will remove unused primer molecules and the template molecule used to create the primer extension product. In some embodiments, the template nucleic acid and all nucleic acid fragments other than the extended primer are removed by exonuclease digestion. In that embodiment, the primer used in the primer extension may have a 5'-end modification making the primer and any extension product resistant to exonuclease digestion. Examples of such modification include phosphorothioate linkage. In other embodiments, RNA template can be removed by enzymatic treatment that will spare DNA, such as RNase digestion, including RNaseH digestion. In yet other embodiments, the primers and large-size template DNA are separated from the extension products by a size-exclusion method, for example, gel electrophoresis, chromatography or isotachophoresis or epitachophoresis.

In some embodiments, purification is by affinity binding. In variations of this embodiment, the affinity is to the specific target sequence (sequence capture). In other embodiments, the primer comprises an affinity tag. Any affinity tag known in the art can be used, such as biotin or an antibody or an antigen for which a specific antibody exists. The affinity partner for the affinity tag may be present in solution, e.g., on a solution-phase solid support, such as suspended panicles or beads, or bound to solid-phase support. In the course of affinity purification, unbound components of the reaction mixture are washed away. In some embodiments, additional steps are taken to remove unused primer. In some embodiments, the affinity capture alters the charge of the primer extension product. For example, the inclusion of one or more biotinylated nucleotides and binding or streptavidin thereto creates an altered charge on the nascent nucleic acid strand. The altered charge can be utilized for separation of the nascent strand (the primer extension product) by isotachophoresis or epitachophoresis.

Notably, methods of the present disclosure do not necessitate a ligation step (e.g., to add common sequences to extended first or second oligonucleotide primers). However, in some embodiments, the invention includes a ligation step. For example, it is possible to add a homopolymer tail to the 3' end of a nucleic acid. In this embodiment, the homopolymer may serve as a binding site for the reverse complement homopolymer (similar to poly-A tail with poly-T primer for mRNA). The ligation adds one or more adapter sequences to the primer extension product generated in the preceding step. The adapter sequence supplies one or more universal priming sites (for amplification or sequencing) and optionally, one or more barcodes. The exact mode of ligating the adapter is immaterial as long as the adapter becomes associated with the primer extension product and enables subsequent steps described below.

In some embodiments described above, the method involves a target-specific primer that includes a universal priming sequence ("priming site") and yields a primer extension product with a single priming site. In such embodiments, only one additional priming sequence ("priming site") needs to be provided to enable exponential amplification. In other embodiments, the target-specific primer does not include a universal priming site. In such embodiments, two priming sites need to be provided to enable exponential amplification. The adapters with universal priming sites may be added by any single-strand ligation methods available in the art.

One example of a single-strand ligation method can be used in embodiments where the extension primer comprises a universal ligation site. In such embodiments, the adapter having a double-stranded region and a single stranded overhang complementary to the universal ligation site in the primer may be annealed and ligated. Annealing of the single stranded 3'-overhang of the adapter to the universal ligation site at the 5'-end of the primer creates a double stranded region with a nick in the strand containing the primer extension product. The two strands can be ligated at the nick by a DNA ligase or another enzyme, or a non-enzymatic reagent that can catalyze a reaction between the 5'-phosphate of the primer extension product and the 3'-OH of the adapter. By connecting the adapter, the ligation provides a universal priming site at one end of the primer extension product.

Another example of a single-strand ligation method can be used to add the universal priming site to the opposite end of the primer extension product (or, in embodiments where the extension primer does not comprise a universal ligation site, to both sides of the extension product). For this embodiment, one or both ends of the primer extension product to be ligated do not have a universal ligation site. Further, in some embodiments, at least one end of the primer extension product to be ligated has an unknown sequence (e.g., due to a random termination event or an unknown sequence variation.). In such embodiment, a sequence-independent single-strand ligation method is employed. An exemplary method is described in a U.S. Application Pub. No. 20140193860. Essentially, the method uses a population of adapters where the single-stranded 3'-end overhang instead of having a universal ligation site, has a random sequence, e.g., a random hexamer sequence. In some embodiments of that method, the adapter also has a hairpin structure. Another example is a method enabled by ACCEL-NGS IS DMA Library Kit (Swift Biosciences, Ann Arbor, Mich.).

The ligation step of the method utilizes a ligase or another enzyme with a similar activity or a non-enzymatic reagent. The ligase can be a DNA or RNA ligase, e.g., of viral or bacterial origin such as T4 or *E. coli* ligase, or thermostable ligases Afu, Taq, Tfl or Tth. In some embodiments, an alternative enzyme, e.g., topoisomerase can be used. Further, a non-enzymatic reagent can be used to form the phosphor-diester bond between the 5'-phosphate of the primer extension product and the 3'-OH of the adapter as described and referenced in U.S. Pat. App. Pub. 2014/0193860 to Bevilacqua et al.

In some embodiments of the method, the first ligation of the adapter is followed by an optional primer extension. The ligated adapter has a free 3'-end that can be extended to create a double-stranded nucleic acid. The end opposite the adapter will then become suitable for a blunt-end ligation of another adapter. Avoiding the need for a single-strand ligation procedure, this double stranded end of the molecule can be ligated to a double stranded adapter by any ligase or another enzymatic or non-enzymatic means. The double stranded adapter sequence supplies one or more universal priming sites (for amplification or sequencing) and optionally, one or more barcodes.

In some embodiments, the method of the invention includes one or more purification steps after the ligation step. The purification will remove unused adapter molecules. The adapters and large-size ligated products are separated from the extension products by a size-exclusion method, for example, gel electrophoresis, chromatography, or isotachophoresis.

In some embodiments, purification is by affinity binding. In variations of this embodiment, the affinity is to the specific target sequence (sequence capture). In other embodiments, the adapter comprises an affinity tag. Any affinity tag known in the art can be used (e.g., biotin or an antibody or an antigen for which a specific antibody exists). The affinity partner for the affinity tag may be associated with a solution-phase support (e.g., on suspended particles or beads), or bound to a solid-phase support. In the course of affinity purification, unbound components of the reaction mixture are washed away. In some embodiments, additional steps are taken to remove unused adapter.

In some embodiments, the invention comprises an amplification step. This step can involve linear or exponential amplification (e.g., PCR). The primers for amplification may include any sequences that are present within the nucleic acid being amplified and can support synthesis of one or both strands. Amplification may be isothermal or involve thermal cycling.

In some embodiments, the amplification is exponential and involves PCR. It is desired to reduce PCR amplification bias. If one or more gene-specific primers are used, to reduced bias, the method involves a limited number of amplification cycles (e.g., about 10 or fewer cycles). In other variations of these embodiments, universal primers are used to synthesize both strands. The universal primer sequences may be a part of the original extension primer of one or both ligated adapters. One or two universal primers can be used. The extension primer and one or both adapters described above can be engineered to have the same primer binding site. In that embodiment, a single universal primer can be used to synthesize both strands. In other embodiments, the extension primer (or adapter) on one side and the adapter on the other side of the molecule to be amplified contain different universal primer binding sites. A universal primer may be paired with another universal primer (of the same or different sequence). In other embodiments, the universal primer may be paired with a gene-specific primer. Because PCR with universal primers has reduced sequence bias, the number of amplification cycles need not be limited to the same extent as in PCR with gene-specific primers. The number of amplification cycles where universal primers are used can be low but also can be as high as about 20, 30 or more cycles.

The invention includes the use of molecular barcodes. The barcodes typically consist of 4 to 36 nucleotides. In some embodiments, barcodes are designed to have a melting temperature within 10° C. or fewer of one another. Barcodes can be designed to form a minimally cross-hybridizing set, i.e., a combination of sequences that under the desired reaction conditions, form as few as possible stable hybrids with one another. Design, placement and use of barcodes for sequence identification and counting and is known in the art. See, for example, U.S. Pat. Nos. 7,393,665, 8,168,385, 8,481,292, 8,685,678, and 8,722,368.

Barcodes can be used to identify each nucleic acid molecule in the sample and its progeny (i.e., a set of nucleic acid molecules that are produced using the original nucleic acid molecule). Such barcodes are "unique IDs" (UIDs).

Barcodes can also be used to identify a sample from which the nucleic acid molecule being analyzed is derived. Such barcodes are "multiplex sample IDs" ("MIDs"). All molecules derived from the same sample share the same MIDs.

Barcodes comprise a unique sequence of nucleotides characteristic of each barcode. In some embodiments, the sequences of barcodes are pre-designed. In other embodiments the barcode sequences are random. All or some nucleotides within the barcode can be random. A random sequence and a random nucleotide base within a known sequence are referred to as "degenerate sequence" and "degenerate base" respectively. In some embodiments, a molecule comprises two or more barcodes; one for molecular identification (UID) and one for sample identification (MID). Sometimes, the UID or the MID each comprise several barcodes that when taken together, enable identification of the molecule or the sample.

In some embodiments, the number of UIDs in the reaction can be in excess of the number of molecules to be labeled. In some embodiments, one or more barcodes are used to group or bin sequences. For example, in some embodiments, one or more UIDs are used to group or bin sequences, wherein the sequences in each bin contain the same UID, i.e., are an amplicons derived from a single target molecule. In some embodiments, UIDs are used to align sequences. In other embodiments, the target-specific region is used to align sequences. In some embodiments of the present invention, UIDs are introduced in the initial primer extension event while the sample barcodes (MIDs) are introduced in the ligated adapters.

After the ligation has been performed, the nucleic acid products can be sequenced. Sequencing can be performed by any method known in the art. Especially advantageous is the high-throughput single molecule sequencing. Examples of such technologies include the 454 LIFE SCIENCES GS FLX platform (454 LIFE SCIENCES) ILLUMINA HISEQ platform (ILLUMINA), ION TORRENT platform (LIFE TECHNOLOGIES), PACIFIC BIOSCIENCES platform utilizing the SMRT sequencing technology (PACIFIC BIOSCIENCES) and any other presently existing or future single-molecule sequencing technology that does or does not involve sequencing by synthesis. In variations of these embodiments, the sequencing utilizes a universal primers site present in one or both adapter sequences or in one or both primer sequences. In yet other variations of these embodiments, a gene-specific primer is used for sequencing. It is noted however, that the universal primers are associated with reduced sequencing bias compared to the gene specific primers.

In some embodiments, the sequencing step involves sequence aligning. In some embodiments, aligning is used to determine a consensus sequence from a plurality of sequences, e.g., a plurality having the same unique molecular ID (UID). In some embodiments, aligning is used to identify sequence variations, such as single nucleotide variations (SNV). In some embodiments, a consensus sequence is determined from a plurality of sequences all having an identical UID. In other embodiments, UID is used to eliminate artifacts, i.e., variations existing in the progeny of a single molecule (characterized by a particular UID). Such artifacts resulting from PCR errors or sequencing errors can be eliminated using UIDs.

In some embodiments, the number of each sequence in the sample can be quantified by quantifying relative numbers of sequences with each UID among the population having the same multiplex sample ID (MID). Each UID represents a single molecule in the original sample and counting different UIDs associated with each sequence variant can determine the fraction of each sequence variant in the original sample, where all molecules share the same MID. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

A sample used in the method of the invention comprises any individual (e.g., human, patient) or environmental sample containing nucleic acids. The polynucleotides can be extracted from the sample, or the sample can be directly subjected to the methods of the invention. The starting sample can also be extracted or isolated nucleic acids, DNA or RNA. The sample can constitute any tissue or fluid obtained from an organism. For example, the sample may be a tumor biopsy or a blood or plasma sample. In some embodiments, the sample is a formalin-fixed, paraffin-embedded (FFPE) sample. The sample may comprise nucleic acids from one or more sources, e.g., one or more patients. In some embodiments, the tissues can be infected with a pathogen and thus contain host's and pathogen's nucleic acids.

Methods of DNA extraction are well-known in the art. See J. Sambrook et al., "Molecular Cloning: A Laboratory Manual," 1989, 2nd Ed., Cold Spring Harbor Laboratory Press: New York. N.Y.). A variety of kits are commercially available for extracting nucleic acids (DNA or RNA) from biological samples (e.g., BD BIOSCIENCES CLONTECH (Palo Alto, Calif.), EPICENTRE TECHNOLOGIES (Madison, Wis.); GENTRA SYSTEMS, INC. (Minneapolis, Minn.); and QIAGEN, INC. (Valencia, Calif.), AMBION, INC. (Austin, Tex.); BIORAD LABORATORIES (Hercules, Calif.); and more.

In some embodiments, the starting sample used in the method of the invention is a library, e.g., a genomic library or an expression library that comprises a plurality of polynucleotides. In other embodiments, a library is created by the method of the invention. With the starting material being a biological sample, the method creates an amplification library, or a collection of amplicons representing variety or sequences. A library can be stored and used multiple times for further amplification or sequencing of the nucleic acids in the library.

Figure 2A:
FIGS. 2A, 2B, 2C, 2D and 2E are a schematic representation of a first embodiment of a method for enrichment of at least one target nucleic acid in a library of nucleic acids according to the present disclosure. In the illustrated embodiment, a first oligonucleotide includes a capture moiety for solution-phase capture of a target nucleic acid.

According to one embodiment of the present disclosure, a method for primer extension target enrichment can include in-solution primer-mediated capture of a target nucleic acid. Turning now to FIGS. 2A-E, a library of nucleic acids includes target nucleic acid 200 including a region of interest (ROI) 202 (FIG. 2A). The target nucleic acid 200 further includes a first end comprising a first adapter 204 and a second end comprising a second adapter 206. In FIGS. 2A-2E, the target nucleic acid 200 is illustrated as a single stranded nucleic acid with the first adapter 204 located at a 3' end (i.e., the first end) of the target nucleic acid 200 and the second adapter 206 located at a 5' end (i.e., the second end) of the target nucleic acid 200. A first oligonucleotide 208 is hybridized to the target nucleic acid 200 in library of nucleic acids. The first oligonucleotide 208 includes a 3' target-specific region 210 that is complementary to the target nucleic acid and a capture moiety 212. In the illustrated embodiment, the target-specific region 210 is complementary to the ROI 202.

Figure 2B:
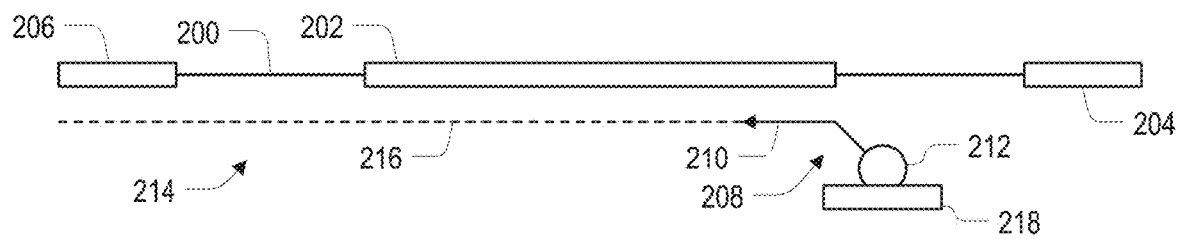

As shown in FIG. 2B, the hybridized first oligonucleotide 208 is extended with a first polymerase (not shown), thereby producing a first primer extension complex 214 comprising the target nucleic acid 200 and the extended first oligonucleotide 216 (with the dashed line indicating the extended portion of the extended first oligonucleotide 216). The first primer extension complex 214 is captured on a solid support 218. The solid support can be a solution-phase support (e.g., a bead or another like particle), or a solid-phase support (e.g., a silicon wafer, a glass slide, or the like). For example, magnetic glass particles and devices employing same described in U.S. Pat. Nos. 656,568, 6,274,386, 7,371,830, 6,870,047, 6,255,477, 6,746,874 and 6,258,531 can be used. In the embodiment illustrated in FIG. 2B, the first primer extension complex 214 is captured on the solid support via the capture moiety 212. Following capture, the first primer extension complex 214 is enriched relative to the library of nucleic acids.

Figure 2C:
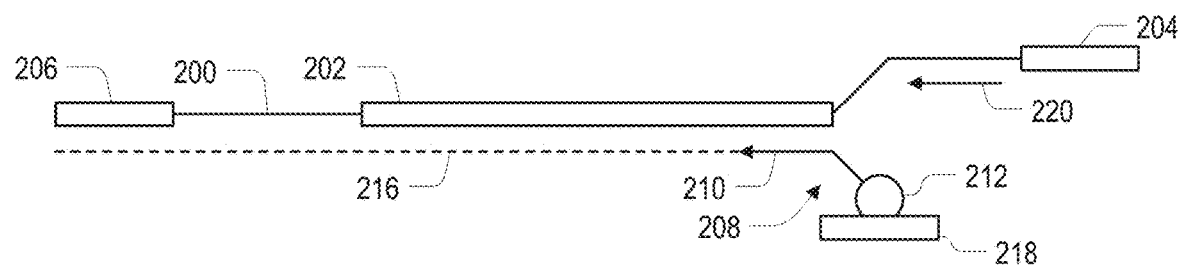

Turning to FIG. 2C, a second oligonucleotide 220 is hybridized to the target nucleic acid 200. The second oligonucleotide 220 is complementary to the target nucleic acid 200 and hybridizes to the target nucleic acid 200 at a 5' position relative to the target specific region 210 of the first oligonucleotide 208. In the illustrated embodiment, the second oligonucleotide 220 is complementary to and hybridizes wish the target nucleic acid 200 at a location just outside of the ROI 202; however, it will be appreciated that the first oligonucleotide 208 and the second oligonucleotide 220 can be designed to hybridize at any defined postilion along the length of the target nucleic acid 200 with the second oligonucleotide 220 hybridizing to the target nucleic acid 200 at a 5' position relative to the target specific region 210 of the first oligonucleotide 208. From FIG. 2C, it can be seen that both the first extended oligonucleotide 216 (which is attached to the solid support 218) and the second oligonucleotide 220 are hybridized to the target nucleic acid 200.

Figure 2D:
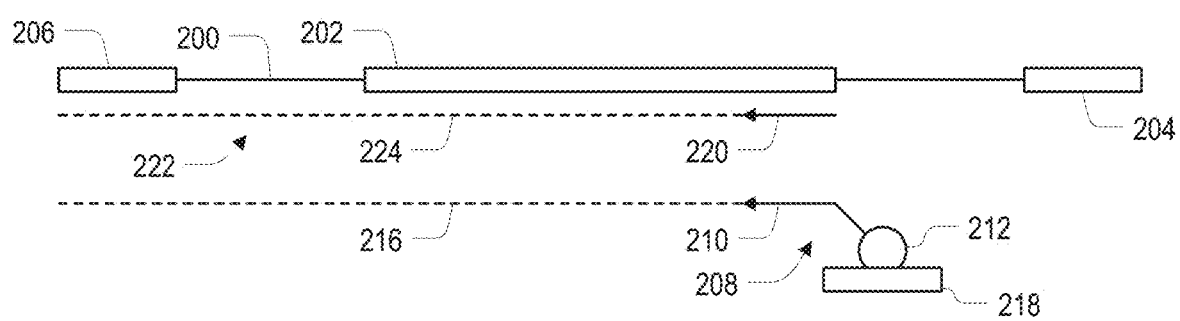

With reference to FIG. 2D, the hybridized second oligonucleotide 220 is extended with a second polymerase (not shown), thereby producing a second primer extension complex 222 including the target nucleic acid 200 and the extended second oligonucleotide 224 (with the dashed line indicating the extended portion of the extended second oligonucleotide 224). In one aspect, extension of the hybridized second oligonucleotide 220 liberates the extended first oligonucleotide 216 from the first primer extension complex 214. In another aspect, the extended first oligonucleotide 216 (including the first oligonucleotide primer 208) remains attached to the solid support 218.

Figure 2E:
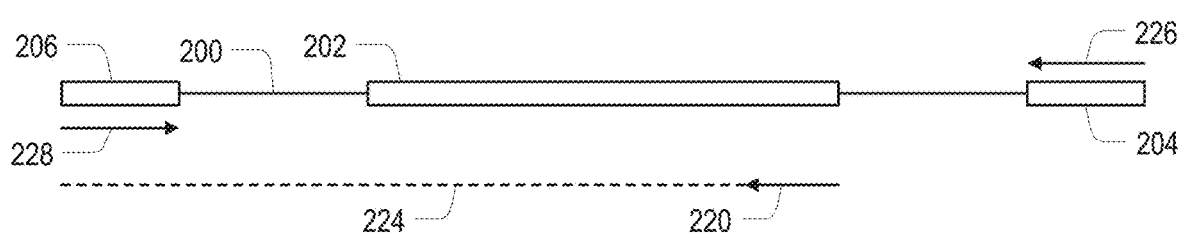

As illustrated in FIG. 2E, the target nucleic acid 200 is amplified with a third polymerase (not shown), a first amplification primer 226, and a second amplification primer 228. The first amplification primer 226 includes a 3' end complementary to the first adapter 204 and the second amplification primer 228 includes a 3' end complementary to the second adapter 206.

Figure 3A:
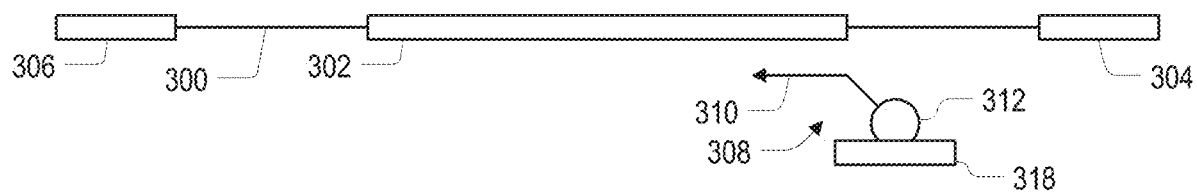
FIGS. 3A and 3B are a schematic representation of yet a second embodiment of a method for enrichment of at least one target nucleic acid in a library of nucleic acids according to the present disclosure. In the illustrated embodiment, a first oligonucleotide is bound to a solid support for in situ capture of a target nucleic acid.
Figure 3B:
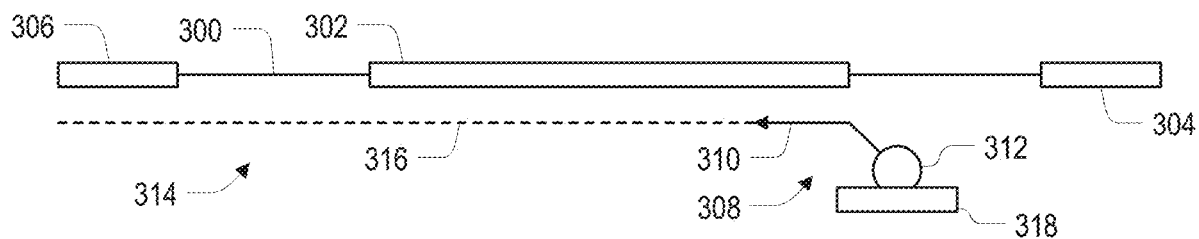

According to another embodiment of the present disclosure, a method for primer extension target enrichment can include in situ primer mediated capture of a target nucleic acid. With reference to FIGS. 3A and 3B, a library of nucleic acids includes target nucleic acid 300 including a region of interest (ROI) 302 (FIG. 3A). The target nucleic acid 300 further includes a first end comprising a first adapter 304 and a second end comprising a second adapter 306. In FIGS. 3A and 3B, the target nucleic acid 300 is illustrated as a single stranded nucleic acid with the first adapter 304 located at a 3' end (i.e., the first end) of the target nucleic acid 200 and the second adapter 306 located at a 5' end (i.e., the second end) of the target nucleic acid 300. A first oligonucleotide 308 is hybridized to the target nucleic acid 300 in library of nucleic acids. The first oligonucleotide 308 includes a 3' target-specific region 310 that is complementary to the target nucleic acid 300 and a capture moiety 312. In the illustrated embodiment, the target-specific region 310 is complementary to the ROI 302.

In comparison with the embodiment illustrated in FIGS. 2A-2E, the first oligonucleotide 308 is captured on a solid support 318 prior to or concurrent with hybridization of the first oligonucleotide 308 to the target nucleic acid 300. The solid support 318 can be a solution-phase support (e. g., a bead or another like particle), or a solid-phase support (e.g., a silicon wafer, a glass slide, or the like). In the embodiment illustrated in FIG. 3A, the first oligonucleotide 308 is captured on the solid support 318 via the capture moiety 312. Turning to FIG. 3B, the hybridized first oligonucleotide 308 is extended with a first polymerase (not shown), thereby producing a first primer extension complex 314 comprising the target nucleic acid 300 and the extended first oligonucleotide 316 (with the dashed line indicating the extended portion of the extended first oligonucleotide 316). Notably, the first primer extension complex 314 is captured on the solid support 318, enabling enrichment of the target nucleic acid 300 relative to the library of nucleic acids. Thereafter, a second primer hybridization and extension reaction can be carried out as illustrated in FIGS. 2C and 2D followed by an amplification step as illustrated in FIG. 2E.

Figure 4A:
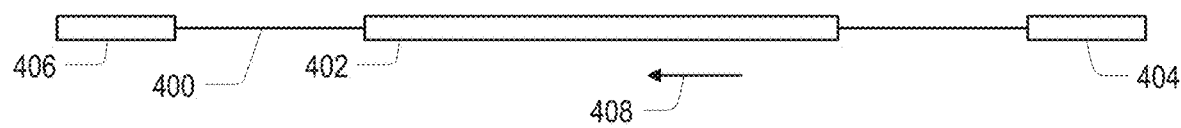
FIGS. 4A, 4B, 4C and 4D are a schematic representation of still a third embodiment of a method for enrichment of at least one target nucleic acid in a library of nucleic acids according to the present disclosure. In the illustrated embodiment, one or mote capture moieties are incorporated during extension of a first oligonucleotide hybridized to a target nucleic acid, thereby enabling capture of a complex including the target nucleic acid and the extended first oligonucleotide on a solid support.

According to yet another embodiment of the present disclosure, a method for primer extension target enrichment can include extension-mediated capture of a target nucleic acid. Referring to FIGS. 4A-4D, a library of nucleic acids includes target nucleic acid 400 including a region of interest (ROI) 402 (FIG. 4A). The target nucleic acid 400 further includes a first end comprising a first adapter 404 and a second end comprising a second adapter 406. In FIGS. 4A-4D, the target nucleic acid 400 is illustrated as a single stranded nucleic acid with the first adapter 404 located at a 3' end (i.e., the first end) of the target nucleic acid 400 and the second adapter 406 located at a 5' end (i.e., the second end) of the target nucleic acid 400. A first oligonucleotide 408 is hybridized to the target nucleic acid 400 in library of nucleic acids. The first oligonucleotide 408 is complementary to the target nucleic acid 400. Notably, the first oligonucleotide 408 does not necessarily include a capture moiety as compared with the first oligonucleotide 208 including capture moiety 212 in FIG. 2A. In the embodiment illustrated in FIG. 4A, the first oligonucleotide 408 is complementary to a portion of the ROI 402.

Figure 4B:
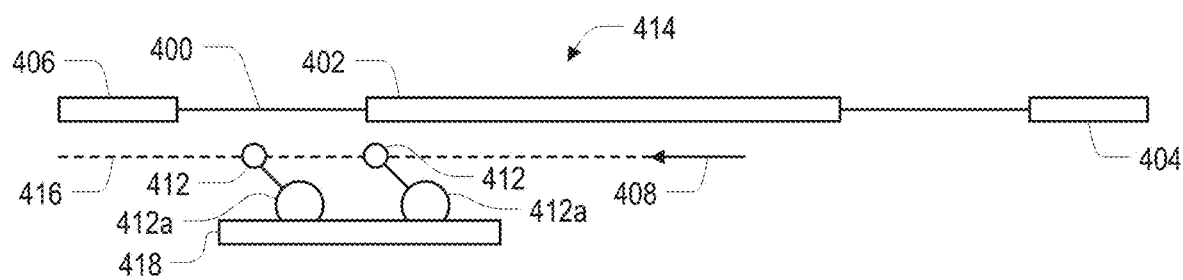

As shown in FIG. 4B, the hybridized first oligonucleotide 408 is extended with a first polymerase (not shown), thereby producing a first primer extension complex 414 comprising the target nucleic acid 400 and the extended first oligonucleotide 416 (with the dashed line indicating the extended portion of the extended first oligonucleotide 416). According to the embodiment illustrated in FIGS. 4A-4D, extension of the first oligonucleotide 408 is performed in the presence of one or more modified nucleic acids 412. Each modified nucleic acid includes a capture moiety 412a or can undergo modification to add a capture moiety 412a concurrent with or subsequent to extension of the first oligonucleotide 416.

The incorporation of one or more modified nucleic acids 412 including capture moieties 412a enables extension-mediated capture of the target nucleic acid 400 on a solid support 418. The solid support 418 can be a solution-phase support (e.g., a bead or another like particle), or a solid-phase support (e.g., a silicon wafer, a glass slide, or the like). In the embodiment illustrated in FIG. 4B, the first primer extension complex 414 is captured on the solid support 418 via the modified nucleic acid 412 including the capture moiety 412a. Following capture, the first primer extension complex 414 is enriched relative to the library of nucleic acids.

Figure 4C:
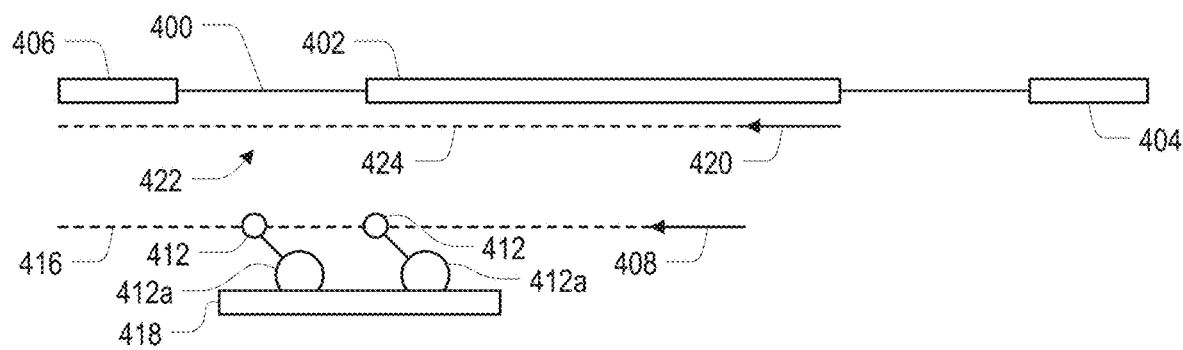

Turning to FIG. 4C a second oligonucleotide 420 is hybridized to the target nucleic acid 400. The second oligonucleotide 420 is complementary to the target nucleic acid 400 and hybridizes to the target nucleic acid 400 at a 5' position relative to first oligonucleotide 408. In the illustrated embodiment, the second oligonucleotide 420 is complementary to and hybridizes with the target nucleic acid 400 at a location just inside the ROI 402; however, it will be appreciated that the first oligonucleotide 408 and the second oligonucleotide 420 can be designed to hybridize at any defined position along the length of the target nucleic acid 400 with the second oligonucleotide 420 hybridizing to the target nucleic acid 400 at a 5' position relative to the target specific region 410 of the first oligonucleotide 408.

With continued reference to FIG. 4C, the hybridized second oligonucleotide 420 is extended with a second polymerase (not shown), thereby producing a second primer extension complex 422 including the target nucleic acid 400 and the extended second oligonucleotide 424 (with the dashed line indicating the extended portion of the extended second oligonucleotide 224). Prior to extension of the second oligonucleotide 420 with the second polymerase, the first extended oligonucleotide 416 (which is attached to the solid support 418) and the second oligonucleotide 420 are each hybridized to the target nucleic acid 400. Extension of the hybridized second oligonucleotide 420 liberates the extended first oligonucleotide 416 from the first primer extension complex 414. In another aspect, the extended first oligonucleotide 416 (including the first oligonucleotide primer 408 and the modified nucleic acids 412) remains attached to the solid support 418.

Figure 4D:
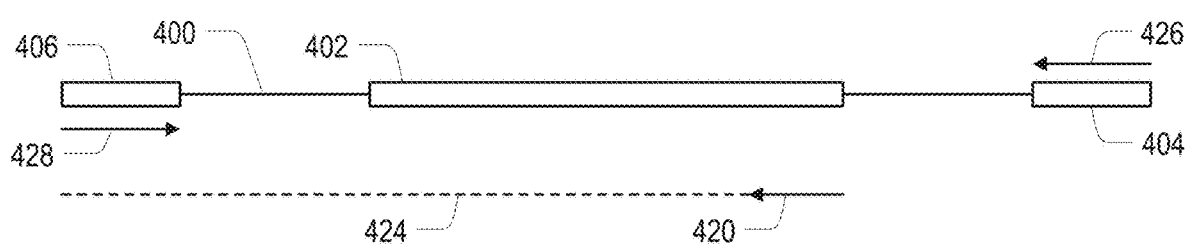

As illustrated in FIG. 4D, the target nucleic acid 400 is amplified with a third polymerase (not shown), a first amplification primer 426, and a second amplification primer 428. The first amplification primer 426 includes a 3' end complementary to the first adapter 404 and the second amplification primer 428 includes a 3' end complementary to the second adapter 406.

Figure 5:
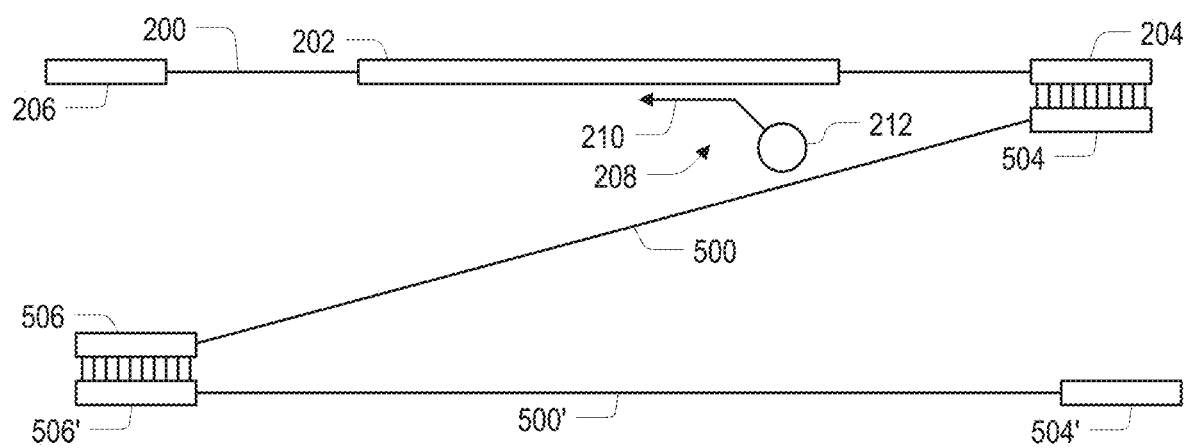
FIG. 5 is a schematic illustration of a plurality of nucleic acids in a library molecules exhibiting intermolecular adapter-adapter hybridization.

In one aspect, target and non-target nucleic acids in a library of nucleic acids can exhibit intermolecular interactions that result in a daisy-chain structure. A shown in FIG. 5, the target nucleic acid 200 (see also FIG. 2A) includes the ROI, the first adapter 204 and the second adapter 206. The first oligonucleotide 208 is hybridized to the target nucleic acid 200. The first oligonucleotide 208 includes the 3' target-specific region 210 and the capture moiety 212. The library of nucleic acids can further include one or more non-target nucleic acids including a first non-target nucleic acid 500 and a second non-target nucleic acid 500'. Similar to the target nucleic acid 200, the first non-target nucleic acid 500 and the second non-target nucleic acid 500' each include a first end comprising a first adapter 504 and 504', respectively, and a second end comprising a second adapter 506 and 506', respectively. In one aspect, the first adapter 204 is at least partially complementary to the first adapter 504, and the second adapter 506 is at least partially complementary to the second adapter 506'. Accordingly, the target nucleic acid 200 can daisy-chain with the non-target nucleic acid 500 and the non-target nucleic acid 500' as illustrated in FIG. 5.

In various situations it can be useful to minimize or eliminate the formation of a daisy chain structure. For example, capture of the target nucleic acid 200 through hybridization and extension of the first oligonucleotide 208 can capture by association the non-target nucleic acid 500 and the non-target nucleic acid 500, which can lead to reduced specificity of the capture and enrichment method. To reduce intermolecular interactions between adapter ends of target and non-target nucleic acids in a library of nucleic acids, blocking oligonucleotide can be hybridized to the adapter end sequences.

To facilitate the reduction of off-target hybridization, blocking oligonucleotides have sequences complementary to the adapters (e.g., the first adapter 204 and the second adapter 206), and hybridize preferentially to these adapter sequences. Blocking oligos can ire used in both single-plex and multiplex formats. In the ease that is desirable to multiplex, a variety of sample index sequences can be incorporated into the adapters. However, this requires the use of a matched blocking oligonucleotide. In the case that a large number of sample indices are used (e.g., 24, 96, etc.), one possibility is to use one "universal" blocking oligonucleotide. The universal blocking oligonucleotide has a unique sequence including non-natural nucleotides that are capable of binding to a large number of different sample index sequences. As a result, only a single blocking oligonucleotide is added to the nucleic acid sample. Alternatively (or in addition), the single universal blocking oligonucleotide can be a mixture of oligonucleotides that collectively make up a universal blocking oligonucleotide composition.

In one aspect, a universal blocking oligonucleotide includes a nonspecific region flanked by first and second specific regions. The nonspecific region includes, for example, a run of inosines that align with the sample index sequence when the universal blocking oligonucleotide is hybridized to the target adapter sequence. The specific regions of the universal blocking oligonucleotide are complementary to the invariant portion of the adapter sequence and include one or more melting temperature ($T_m$) modified bases to increase the $T_m$ of the blocking oligonucleotide-adapter duplex. Examples of $T_m$-modified base substitutes are illustrated in Table 1.

TABLE 1

| Standard NTP | $T_m$-modified substitute base |
|---|---|
| ATP | 8-aza-7-Br-7-deaza-2,6-diaminopurine |
| CTP | 5-propynyl-dC |
| GTP | 8-aza-7-Br-7-deaza-dG |
| TTP | 5-propynyl-dU |

In another aspect, unamplified nucleic acid libraries prepared with two different adapter sequences could be processed without blocking oligonucleotides if the adapter ends do not hybridize to one another. Adapter types suitable for this approach include forked and Y-shaped adapters.

EXAMPLES

Example 1

Primer Extension Target Enrichment with In-Solution Primer-Mediated Capture (PETE-Cap)

Figure 6A:
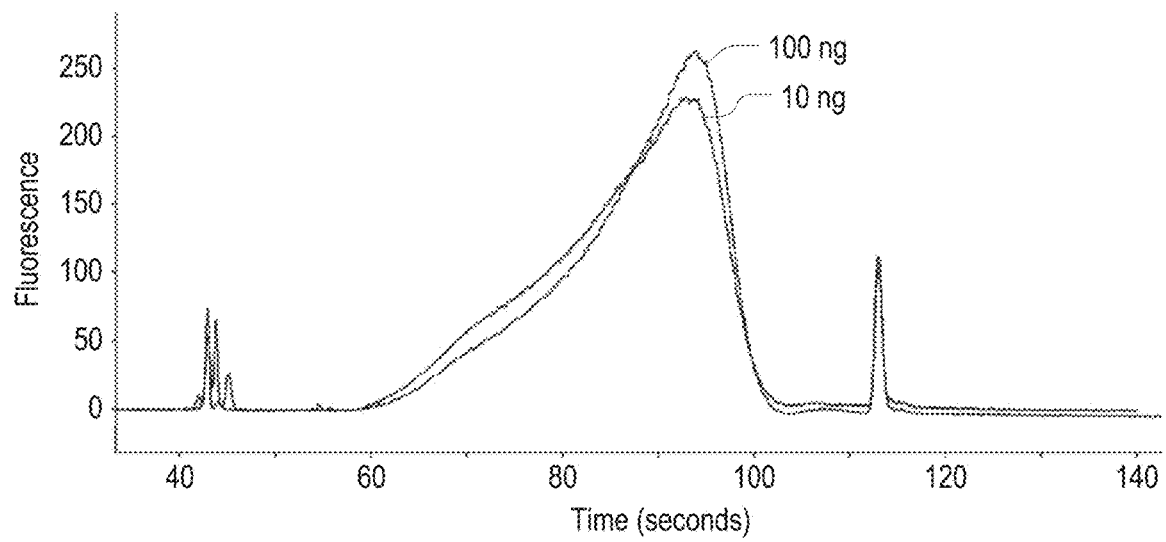
FIG. 6A is a fluorescence output trace from an electrophoretic DMA analyzer for libraries of nucleic acids derived from human genomic DNA and adapted with common adapter end sequences using a commercial library preparation kit. Data was collected following standard PCR amplification of 1 µL of a 10 ng library and 1 µL of a 100 ng library for 5 and 12 cycles, respectively. Libraries of nucleic acids were sample and enriched for target nucleic acids according to the present disclosure.

Primer extension target enrichment with in-solution primer-mediated capture was implemented according to the following protocol. Duplicate libraries of nucleic acids were prepared from 10 ng and 100 ng of NA12878 Human Genomic DNA (CORIELL), using a KAPA HYPERPLUS library preparation kit according to the manufacturer's instructions, up to and including the 0.8× post-ligation clean-up step (FIG. 6A). Thereafter, target nucleic acids in the library of nucleic acids were enriched for by primer extension target enrichment including in-solution primer-mediated capture according to the embodiment illustrated in FIG. 2. Primers complimentary to the plus or minus strand of a target nucleic acid were designed for the same exon of each gene (i.e., target) of interest. The first (inner) oligonucleotide primers were 20-25 nucleotides long and the second (outer) oligonucleotide primers were 50-60 nucleotides long. The additional length associated with the second oligonucleotide primers (as compared with the first oligonucleotide primers) was due to the inclusion of a 5' non-complementary tail sequence. Notably, the 5' non-complementary tail sequence can be omitted in order to reduce the overall length of the second oligonucleotide primers.

The first oligonucleotide (inner) primer hybridization and extension reaction was set up according to Table 2. The library of nucleic acids was consisted of the unamplified product prepared with the KAPA HYPERPLUS library preparation kit as described above. The total volume of the library of nucleic acids recovered following elution after the 0.8× post-ligation clean-up step was included in the reaction; the final concentration of the library of nucleic acids was not determined (n. d.). The Mastermix consisted of a custom KAPA 2G polymerase PCR Mastermix. The primer mixture consisted of a set of 377 first oligonucleotide target specific inner primers present at an equimolar concentration. Notably, each of the first oligonucleotide target specific inner primers included a 5' biotin capture moiety.

TABLE 2

| Component | Volume (µL) | Final Concentration |
|---|---|---|
| Library of nucleic acids | total eluate | n.d. |
| Mastermix | 10 | 1X |
| Primer Mixture | 1.5 | 300 nM total, 0.81 nM each |
| Water | to 50 µL | — |

The first oligonucleotide primers were hybridized to the target nucleic acids in the library of nucleic acids and extended with a polymerase according to the thermal profile in Table 3 for a total time of about 1 hour. Notably, the protocol in Table 3 omits the use of thermal cycling.

TABLE 3

| Step | Temp (° C.) | Time (min:sec) | Ramp Rate |
|---|---|---|---|
| Denaturation | 95 | 5:00 | Standard to 80° C. |
|  | 80 | 0:01 | 0.4% to 60 or 65° C. |
| Hybridization | 60 or 65 | 10:00 | Standard to 65° C. |
| Extension | 65 | 2:00 | Standard to 4° C. |
|  | 4 | HOLD | — |

Following hybridization and extension with the biotinylated first oligonucleotide primers, samples were mixed at a 1:1 ratio with DYNABEADS MYONE streptavidin T1 capture beads (THERMO FISHER SCIENTIFIC). Capture beads were prepared prior to addition to DNA samples by washing twice with 1× binding and wash buffer, and resuspending in 2× binding and wash buffer. The composition of the binding and wash buffer is listed in Table 4.

TABLE 4

| Component | Final Concentration (1X) |
| --- | --- |
| Tris-Cl—HCl (pH 7.5) | 20 mM |
| EDTA | 1 mM |
| NaCl | 1M |
| Tween | 0.1% |
| Water | — |

Samples were incubated with 50 µL MYONE capture beads for 10 minutes at room temperature on an automated sample rotator. Once biotinylated DNA had bound to beads, samples were placed on a magnet for 3 minutes to capture the beads and the supernatant was removed and discarded. Beads were washed twice, once with the 1× binding and wash buffer described in Table 3, and once with 10 mM Tris-HCl at pH 8.0, to remove non-biotinylated DNA. Beads were then resuspended in 20 µL of 10 mM Tris-Cl at pH 8.0.

Resuspended beads were added to a second oligonucleotide (outer) primer hybridization reaction mixture according to Table 5.

TABLE 5

| Component | Volume (µL) | Final Concentration |
| --- | --- | --- |
| DNA + Beads | 20 | n.d. |
| KAPA 2G Buffer A | 10 | 1X |
| Prime Mixture | 2 | 4 µM total, 10.8 nM each |
| Water | to 50 µL | — |

The reaction mixture listed in Table 5 was incubated at 55° C. for 165 minutes to enable the second oligonucleotide primers to hybridize to the target nucleic acids in the library of nucleic acids, allowing for increased specificity of target capture.

Samples were then washed and eluted as described previously (i.e., a single wash with 1× binding and wash buffer and a single wash with 10 mM Tris-HCl, followed by resuspension in 20 µL 10 mM Tris-HCl).

Resuspended beads were added into a second extension reaction, resulting in extension of the second oligonucleotide winter and liberation of the target nucleic acid molecules into solution. The composition of the second extension reaction is hated in Table 6.

TABLE 6

| Component | Volume (µL) | Final Concentration |
| --- | --- | --- |
| DNA + Beads | 20 | n.d. |
| KAPA 2G PCR kit Buffer A | 10 | 1X |
| dNTPs | 1 | 0.2 mM each |
| KAPA 2G Fast DNA Polymerase | 1 | 5 U |
| Water | to 50 µL | — |

Following the second extension reaction, samples were incubated at 50° C. for 2 minutes and were then placed directly onto a magnet on ice for 1 minute. The supernatant was removed from the sample (without disturbing the beads) and added to an equal volume of KAPA PURE BEADS capture beads (KAPA BIOSYSTEMS). A 1× clean-up was performed and samples were eluted in 15 µL 10 mM Tris-Cl, pH 8.0.

Figure 6B:
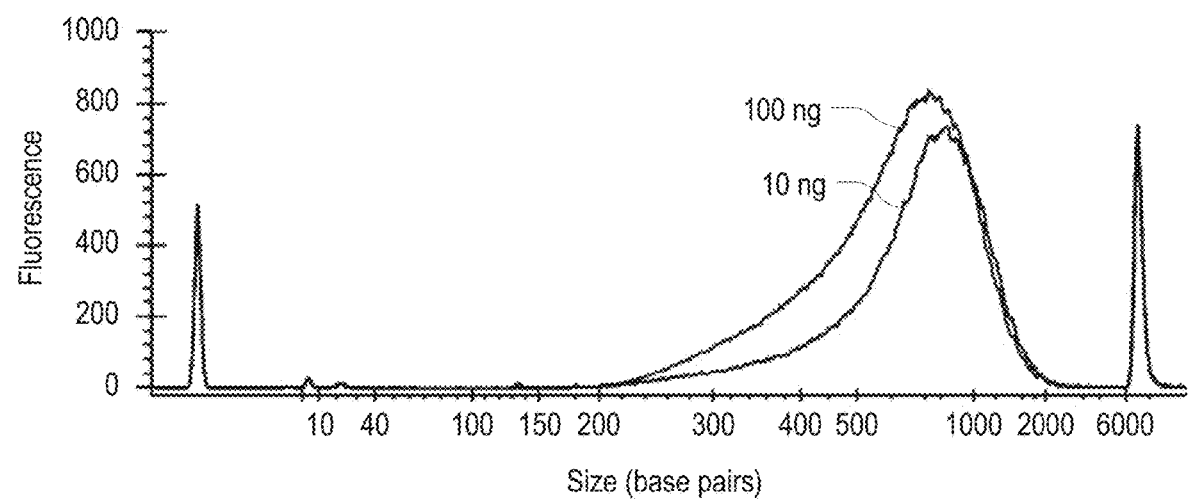
FIG. 6B is a fluorescence-based size analysis of the libraries of nucleic acids of FIG. 6A following primer extension target enrichment and amplification according to the present disclosure.
Figure 7:
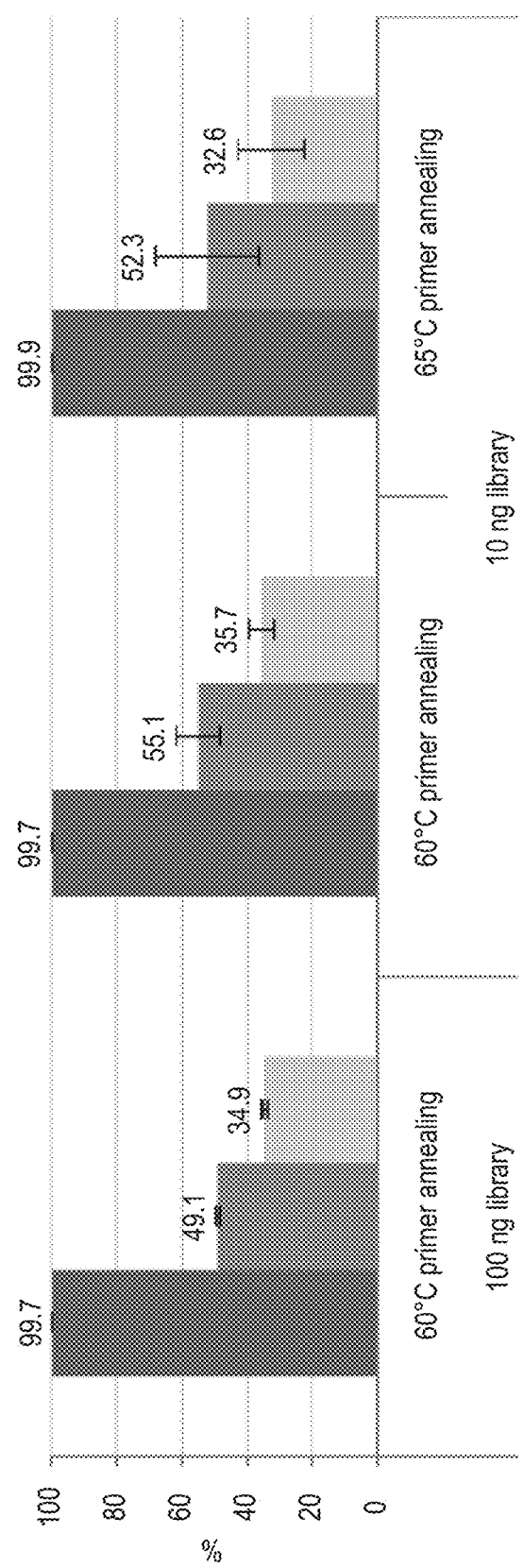
FIG. 7 is a bar chart depicting high level sequencing metrics for the enriched libraries of nucleic acids of FIG. 6B. Greater than 99% of sequencing reads mapped to sequences known to be present in the libraries and about half of the sequencing reads mapped to the target nucleic acids enriched for. The fold-80 base penalty for the libraries was 1.4 and 1.5 for the 60° C. and 65° C. first oligonucleotide primer annealing temperatures, respectively. Within each cluster of three bars, data is shown for percent trimmed reads mapped (left), percent bases in padded target nucleic acid (center), and percent mapped non-duplicate reads on-target (right).

A next step of the target enrichment protocol was an amplification reaction and KAPA PURE BEAD capture bead (KAPA BIOSYSTEMS) clean up, according to the manufacturer's instructions for the KAPA HYPERPLUS library preparation kit. The final product was eluted in 25 µL Tris-HCl. The enriched target nucleic acids were then amplified and purified using a KAPA HYPERPLUS library preparation kit (KAPA BIOSYSTEMS) according to the manufacturer's instructions (FIG. 6B). Enriched, amplified libraries were sequenced on a MINISEQ DNA sequencer (ILLUMINA) using a mid-output kit with 2 by 150 bp reads, 1.6 pM loading concentration, and 1% PhiX DNA. The resulting sequencing data was processed using a pipeline developed for analysis of SEQCAP EZ target enrichment system (ROCHE) data in order to assess the extent of target enrichment (FIG. 7).

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

The invention claimed is:

1. A method for enrichment of at least one target nucleic acid in a library of nucleic acids, wherein the method comprises the following steps:
   (a) hybridizing a first oligonucleotide to a target nucleic acid in the library of nucleic acids, wherein each of the nucleic acids in the library of nucleic acids has a first end comprising a first adapter and a second end comprising a second adapter;
   (b) extending the hybridized first oligonucleotide with a first polymerase, thereby producing a first primer extension complex, wherein the first primer extension complex comprises the target nucleic acid and the extended first oligonucleotide;
   (c) capturing the first primer extension complex;
   (d) enriching the first primer extension complex relative to the library of nucleic acids;
   (e) hybridizing a second oligonucleotide to the target nucleic acid;
   (f) extending the hybridized second oligonucleotide with a second polymerase, thereby producing a second primer extension complex, wherein the second primer extension complex comprises the target nucleic acid and the extended second oligonucleotide, thereby liberating the extended first oligonucleotide from the first primer extension complex; and
   (g) amplifying the target nucleic acid with a third polymerase, a first amplification primer, and a second amplification primer, wherein the first amplification primer has a 3' end complementary to the first adapter and the second amplification primer has a 3' end complementary to the second adapter, wherein the step of amplifying the target nucleic acid produces a copy of target nucleic acid, wherein the copy of the target nucleic acid comprises the entire sequence of the target nucleic acid, and wherein the copy of the target nucleic acid is of greater length than the extended first oligonucleotide and the extended second oligonucleotide.

2. The method of claim 1, further comprising sequencing the amplified target nucleic acid.

3. The method of claim 1, wherein the first oligonucleotide comprises a capture moiety.

4. The method of claim 1, wherein the first oligonucleotide is bound to a solid support prior to hybridizing the first oligonucleotide to a target nucleic acid, and wherein hybridizing the first oligonucleotide to the target nucleic acid and extending the hybridized first oligonucleotide with a polymerase thereby captures the first primer extension complex on the solid support.

5. The method of claim 1, further comprising incorporating at least one modified nucleotide into at least one of the extended first oligonucleotide in the first primer extension complex and the extended second oligonucleotide in the second primer extension complex.

6. The method of claim 1, further comprising incorporating at least one modified nucleotide into the extended first oligonucleotide in the first primer extension complex, the at least one modified nucleotide having a capture moiety.

7. The method of claim 1, further comprising incorporating at least one uracil into at least one of:
the extended first oligonucleotide in the first primer extension complex, and the extended second oligonucleotide in the second primer extension complex, thereby forming a uracil-containing oligonucleotide product.

8. The method of claim 1, further comprising contacting the library of nucleic acids with a blocking oligonucleotide.

9. The method of claim 1, wherein the first adapter and the second adapter are forked adapters.

10. The method of claim 1, wherein the first adapter and the second adapter comprise at least one uracil.

11. The method of claim 1, wherein the second oligonucleotide hybridizes to the target nucleic acid at a position 5' to the first oligonucleotide.

12. The method of claim 1, wherein at least one of the first adapter, the second adapter, the first amplification primer, and the second amplification primer comprises at least one of a unique identifier (UID) sequence, or a molecular identifier (MID) sequence.

* * * * *